US009833591B1

(12) United States Patent
Ormrod

(10) Patent No.: US 9,833,591 B1
(45) Date of Patent: Dec. 5, 2017

(54) FLOW INTERRUPTER FOR RESPIRATORY TREATMENT APPARATUS

(71) Applicant: ResMed Limited, Bella Vista (AU)

(72) Inventor: Joseph Samuel Ormrod, Surry Hills (AU)

(73) Assignee: ResMed Limited (AU)

( * ) Notice: Subject to any disclaimer, the term of this patent is extended or adjusted under 35 U.S.C. 154(b) by 929 days.

(21) Appl. No.: 13/713,478

(22) Filed: Dec. 13, 2012

Related U.S. Application Data

(60) Provisional application No. 61/582,982, filed on Jan. 4, 2012.

(51) Int. Cl.

| A61M 16/20 | (2006.01) |
|---|---|
| A61M 16/00 | (2006.01) |
| A61M 16/08 | (2006.01) |
| A61M 39/10 | (2006.01) |
| F16L 27/107 | (2006.01) |
| F16K 7/08 | (2006.01) |

(52) U.S. Cl.
CPC ......... *A61M 16/20* (2013.01); *A61M 16/0816* (2013.01); *A61M 16/0875* (2013.01); *A61M 39/1055* (2013.01); *A61M 2205/0216* (2013.01); *A61M 2205/3334* (2013.01); *A61M 2205/582* (2013.01); *F16K 7/08* (2013.01); *F16L 27/107* (2013.01)

(58) Field of Classification Search
CPC . F16K 7/04; F16K 7/08; A61F 5/4405; A61B 17/3462; A61M 39/0613; A61M 16/20
USPC ........ 128/205.24; 251/342, 4, 340; 604/250, 604/34, 248, 167, 246, 256, 264, 350, 604/323, 326, 537, 544, 32; 137/614, 14
See application file for complete search history.

(56) References Cited

U.S. PATENT DOCUMENTS 2,844,351 A * 7/1958 Smith ............... A61M 5/16881
                                                    251/340
3,329,390 A * 7/1967 Hulsey ............................. 251/4
(Continued)

FOREIGN PATENT DOCUMENTS

| GB | 326546 A * | 3/1930 | ............... F16K 7/08 |
|---|---|---|---|
| SE | WO 2004023047 A1 * | 3/2004 | ............... F16K 7/08 |
| SE | EP 2492606 A1 * | 8/2012 | ............... F24F 13/10 |

*Primary Examiner* — Lynne Anderson
*Assistant Examiner* — Joseph D Boecker
(74) *Attorney, Agent, or Firm* — Lerner, David, Littenberg, Krumholz & Mentlik, LLP

(57) ABSTRACT

A flow interrupter for gas flow delivered by a delivery conduit in a respiratory treatment system permits temporary interruption of flow in the conduit. Typically, the apparatus has a passage to conduct a breathable gas. The passage traverses through a flexible wall such as a stretchable sleeve. The flexible wall may include a first and second ends. A manipulator may be attached to the flexible wall. The flexible wall sleeve may be adapted to twistably collapse between the first and second ends so as to reduce the passage of the channel by operation of the manipulator. The flow interrupter may be formed with a swivel and operation of the sleeve may be implemented by rotation of the swivel. Sufficient rotation of such a swivel may form a vortex closure of material to close the channel. Release of the manipulator may then permit unwinding of the vortex closure, re-opening the channel.

29 Claims, 6 Drawing Sheets

(56) References Cited

U.S. PATENT DOCUMENTS

| | | | | | |
|---|---|---|---|---|---|
| 3,383,131 | A | * | 5/1968 | Rosfelder | E21B 25/06 175/240 |
| 4,292,969 | A | * | 10/1981 | Raible | A61M 39/28 251/340 |
| 4,523,737 | A | * | 6/1985 | Wentworth | F16K 7/08 251/213 |
| 5,464,189 | A | * | 11/1995 | Li | 251/4 |
| 8,118,275 | B2 | * | 2/2012 | Mialhe | A61B 17/3462 251/294 |
| 8,656,913 | B2 | * | 2/2014 | Kroupa | 128/204.18 |
| 2007/0163598 | A1 | * | 7/2007 | Chang | A61M 16/00 128/207.16 |

* cited by examiner

FLOW INTERRUPTER FOR RESPIRATORY TREATMENT APPARATUS

CROSS-REFERENCE TO RELATED APPLICATION

The present application claims the benefit of the filing date of U.S. Provisional Patent Application No. 61/582,982 filed Jan. 4, 2012, the disclosure of which is hereby incorporated herein by reference.

FIELD OF THE TECHNOLOGY

The present technology relates to regulating the gas flow delivered to a patient by way of respiratory treatment systems used for delivering of, for example, Non-invasive Positive Pressure Ventilation (NPPV), pressure support ventilation or continuous positive airway pressure (CPAP) therapy for sleep disordered breathing (SDB) conditions such as obstructive sleep apnea (OSA).

BACKGROUND OF THE TECHNOLOGY

Treatment of respiratory disorders, such as obstructive sleep apnea (OSA), with a continuous positive airway pressure (CPAP) flow generator system or treatments of respiratory insufficiency with a ventilator flow generator system, typically involve a delivery of air (or other breathable gas) at pressures above atmospheric pressure to the airways of a patient via a conduit and/or a respiratory mask. Typically, the mask fits over the mouth and/or nose of the patient, or may be an under-nose style mask such as a nasal pillows or nasal cushion style mask.

The associated respiratory treatment systems typically include a flow generator, an air filter, a respiratory mask or cannula, an air delivery conduit connecting the flow generator to the mask, one or more sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors may measure, amongst other things, motor speed, gas volumetric flow rate and outlet pressure, such as with a pressure transducer, flow sensor or the like. The apparatus may optionally include a humidifier and/or heater elements in the path of the air delivery circuit. The controller may include data storage capacity with or without integrated data retrieval/transfer and display functions.

For a patient receiving a pressurized respiratory treatment from such a flow generator, such as a CPAP treatment, bi-level pressure treatment, a pressure support ventilation treatment, etc., and wearing a mask, speaking can be difficult. A non-interrupted gas from the flow generator that enters a patient's mouth and lungs can impede vocalization. In such situations, a patient must either remove his/her mask or turn the flow generator off.

It may be desirable to develop further apparatus to improve patient comfort or convenience when using a respiratory treatment system.

SUMMARY OF THE TECHNOLOGY

One aspect of the present technology relates to an interrupter assembly for reducing or interrupting the gas flow provided to a patient by a respiratory treatment system.

Another aspect of the present technology involves an interrupter assembly for reducing or interrupting the gas flow provided to a patient by a respiratory treatment conduit.

A still further aspect of the present technology involves a swivel for a respiratory treatment conduit.

A still further aspect of the present technology involves a swivel configured as a flow interrupter for reducing or interrupting the gas flow provided to a patient by way of a conduit associated with the swivel.

In an example embodiment of the present technology, an apparatus may be arranged for inclusion in a gas supply channel of a respiratory treatment system to selectively interrupt a flow of a breathable gas through the channel. The apparatus may include a swivel including first and second swivel members arranged for rotation with respect to each other. It may further include a flexible wall comprising a first end and a second end, each end being attached to a respective swivel member. The flexible wall may be arranged to, upon inclusion of the apparatus with the respiratory treatment system, form a portion of the gas supply channel. In some such cases, the apparatus may be configured such that a rotation of one of the swivel members with respect to the other collapses the flexible wall between the first and the second end to reduce or interrupt the gas flow through the gas supply channel.

In some such embodiments of the apparatus, the flexible wall may be formed by a sleeve. The flexible wall may be configured to twist with rotation of the swivel to reduce the gas flow through the channel. In some such cases, the flexible wall may be configured to twist with rotation of the swivel to close the channel and interrupt the gas flow through the channel. Optionally, such a flexible wall may be configured to stretch with rotation of the swivel members with respect to each other. Still further, the flexible wall may be formed of a resilient material and the flexible wall may be configured to untwist by an elastic force of the material.

In some such embodiments, the first swivel member may be formed as an inner cylindrical member and the second swivel member may be formed as an outer cuff member. Optionally, the cuff member may be adapted to retain a portion of the inner cylindrical member. The first end of the flexible wall may be fixed to the inner cylindrical member and the second end of the flexible wall may be fixed to the outer cuff member. In some such embodiments, the apparatus may further include a coupler for coupling with a breathable gas inlet of a patient interface, such as a respiratory mask. In some embodiments of such apparatus, it may further include a connector for coupling with a breathable gas outlet of a flow generator.

In some such cases, the swivel may include a lock to selectively prevent rotation of the swivel members. Optionally, in some cases the apparatus may be integrally connected to a conduit arranged for connection to an inlet of a patient interface or an outlet of a flow generator. In some cases, the flexible wall and swivel may be adapted to collapse the flexible wall to form a bound vortex closure of flexible wall material. In some embodiments, at least one of the members may include a protrusion arranged to facilitate a single handed manipulation of the apparatus.

Some embodiments of the present technology may include an apparatus for selectively interrupting a flow of a breathable gas through a respiratory conduit. The apparatus may include a conduit having a passage to conduct a breathable gas through a flexible wall sleeve with a first end and a second end. The apparatus may also include a manipulator attached to the flexible wall. In some such cases, the flexible wall sleeve may be adapted to twistably collapse between the first and second ends so as to reduce the passage by operation of the manipulator.

In some such embodiments, the manipulator may include a swivel. The swivel may optionally include an inner cylindrical member and an outer cuff member. The inner member and outer member may be adapted for relative rotation. Optionally, the cuff member may be adapted to retain a portion of the inner cylindrical member. In some embodiments, the first end of the flexible wall sleeve may be fixed to the inner cylindrical member and the second end of the flexible wall may be fixed to the outer cuff member. The flexible wall sleeve may be configured to twist with rotation of the manipulator to reduce the passage. The flexible wall sleeve may also be configured to twist with rotation of the manipulator to close the passage. Optionally, the flexible wall sleeve may be configured to stretch with rotation of the manipulator. In some such cases, the flexible wall may be formed of a resilient material, and may be configured to untwist by a resiliency force of the material.

In some such embodiments, the apparatus may also include a coupler for coupling with a breathable gas inlet of a patient interface such as a respiratory mask. The apparatus may also include a connector for coupling with a breathable gas outlet of a respiratory treatment apparatus that includes a flow generator. In some cases, the manipulator may include a lock to selectively prevent rotation of the manipulator. Optionally, the conduit may be formed at an outlet of a flow generator of a respiratory treatment apparatus. Still further, in some such cases the flexible wall and manipulator may be adapted to collapse the flexible wall to form a bound vortex closure of stretched wall material.

Additional features of the present respiratory technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
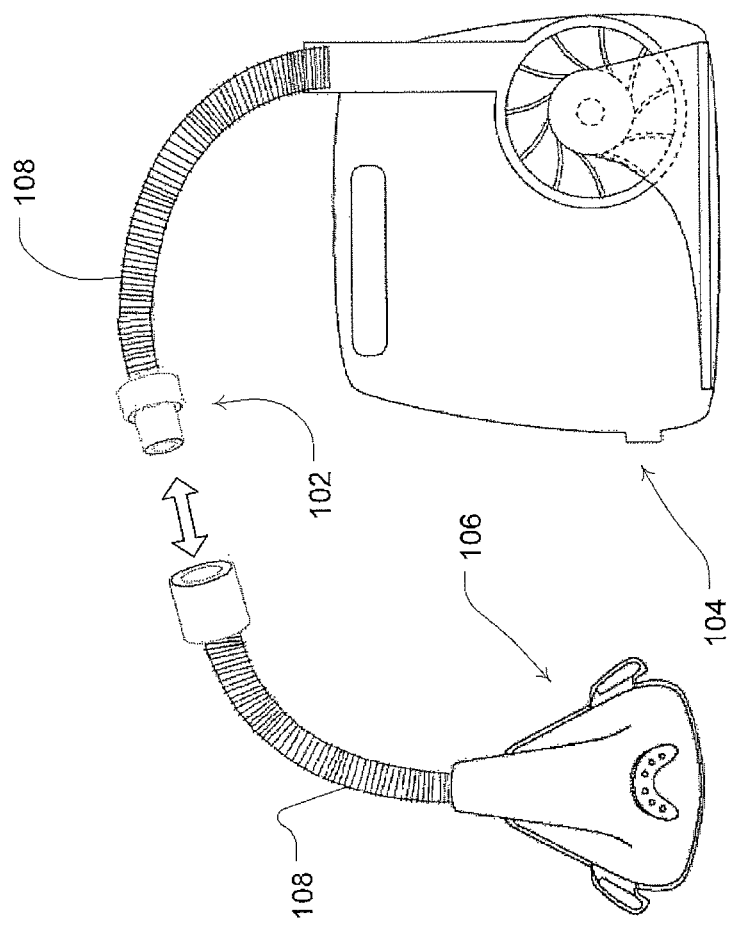
FIG. 1 shows an example flow interrupter of the present technology with a respiratory treatment system.

As illustrated in FIG. 1, embodiments of the present technology may include a flow interrupter 102 for a respiratory treatment system comprising the flow generator 104, such as a ventilator or CPAP device. In a typical system, such as the one illustrated in FIG. 1, the flow interrupter may be included in a channel of a gas communication circuit between a patient interface 106 and the flow generator (e.g., servo-controlled motorized blower) 104. For example, the patient interface may include a supply conduit 108 from the flow generator that supplies a flow of breathable gas to the respiratory system of the patient. The flow interrupter 102 may be integrated or coupled, such as with one or more adapters or connectors, within such a supply conduit as illustrated in FIG. 1. Typically, the patient interface 106 may be a respiratory mask, which may be a nose and mouth mask or full-face mask. However, the flow interrupter may also be implemented with a nasal mask, nasal pillows, nasal cannula, tracheal tube or other device that may provide a seal with at least a portion of the patient's respiratory system so as to permit a pressure treatment at one or more pressures above atmospheric or ambient pressure.

In a typical embodiment, operation of the flow interrupter 102, such as with a manipulator of the flow interrupter 102, will permit a reduction or closing of the passage of the gas/air supply channel between the patient interface and the flow generator. This may reduce or prevent the gas flow from the flow generator to the patient interface and may be accomplished without removal of the patient interface or adjustment to the control or power of the flow generator. For example, in the event a patient wearing a mask wishes to speak without removing a mask or depowering the flow generator, the patient may simply operate the flow interrupter so as to stop a flow of pressurized air through the passage of the supply channel to the mask to permit the patient to talk. When the patient is finished talking, the patient may then release or adjust the flow interrupter so that the supply channel may be re-opened to the mask such that the patient may resume receiving the pressure or flow treatment.

FIG. 1 illustrates the flow interrupter 102 as a component of a respiratory treatment system. In particular, the flow interrupter 102 is integrated on an output conduit of the flow generator 104. At the same time, it serves as a coupler or adapter for or between one or more conduits included within the respiratory treatment system. In other embodiments the flow interrupter 102 may be still an integral part of a conduit, but may be configured to engage with the gas outlet of the apparatus 104 or the gas inlet of the patient interface 106. Alternatively, the flow interrupter 102 may be a separate component configured to engage with respective conduits or inlets/outlets.

Figure 2:
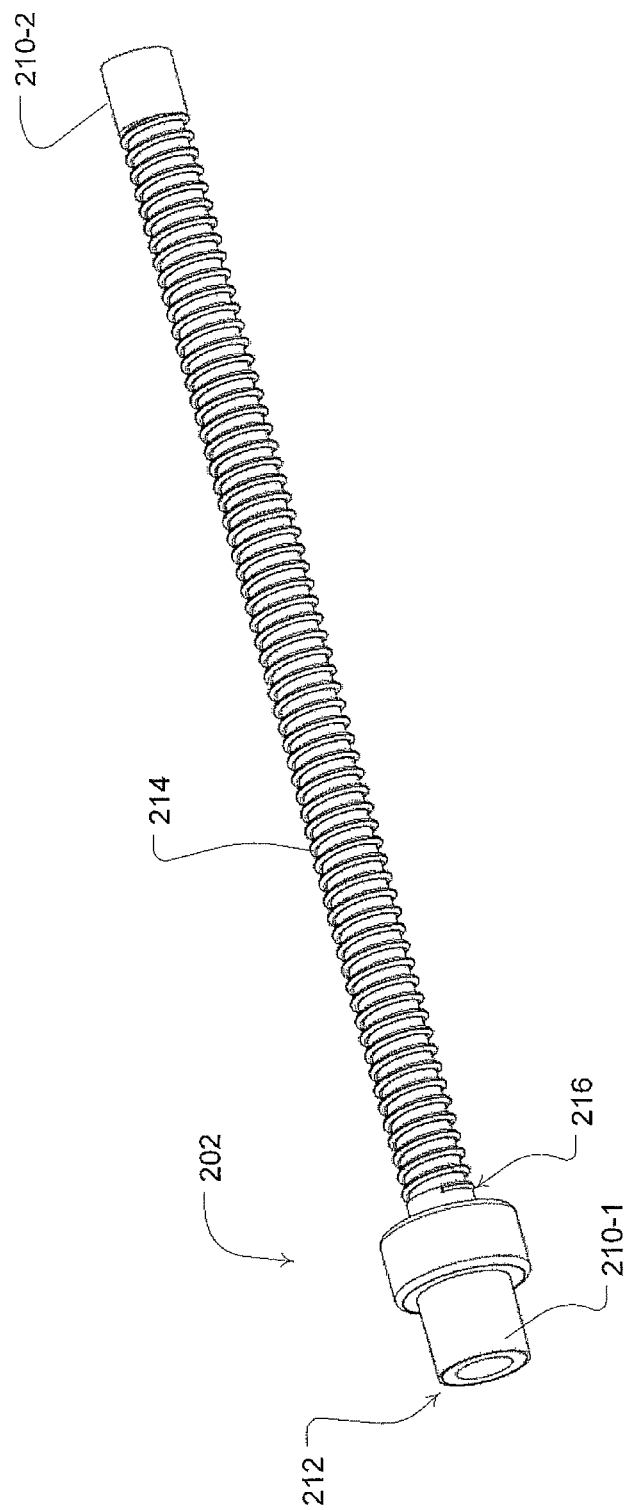
FIG. 2 is an illustration of a flow interrupter of the present technology coupled with a gas supply conduit.

For example, a conduit configuration of the flow interrupter 202 is illustrated in FIG. 2. In this configuration, the flow interrupter 202 serves as a coupler or adapter 210-1 at a first end 212, such as for connection with the inlet of a patient interface. An optional flexible conduit 214 extension may be attachable to or integrated with an opposing end 216 of the flow interrupter 202. The flexible conduit 214 extension may then include a further coupler or connector 210-2, such as for connection with an outlet of the flow generator 104. In such a case, the flow interrupter 202 may be readily implemented with different masks and flow generators. Operation of the flow interrupter 202 may then serve to selectively permit or prevent flow through the flexible conduit 214 extension as well as the conduit channel within the flow interrupter when the interrupter is operated by a user.

Figure 3:
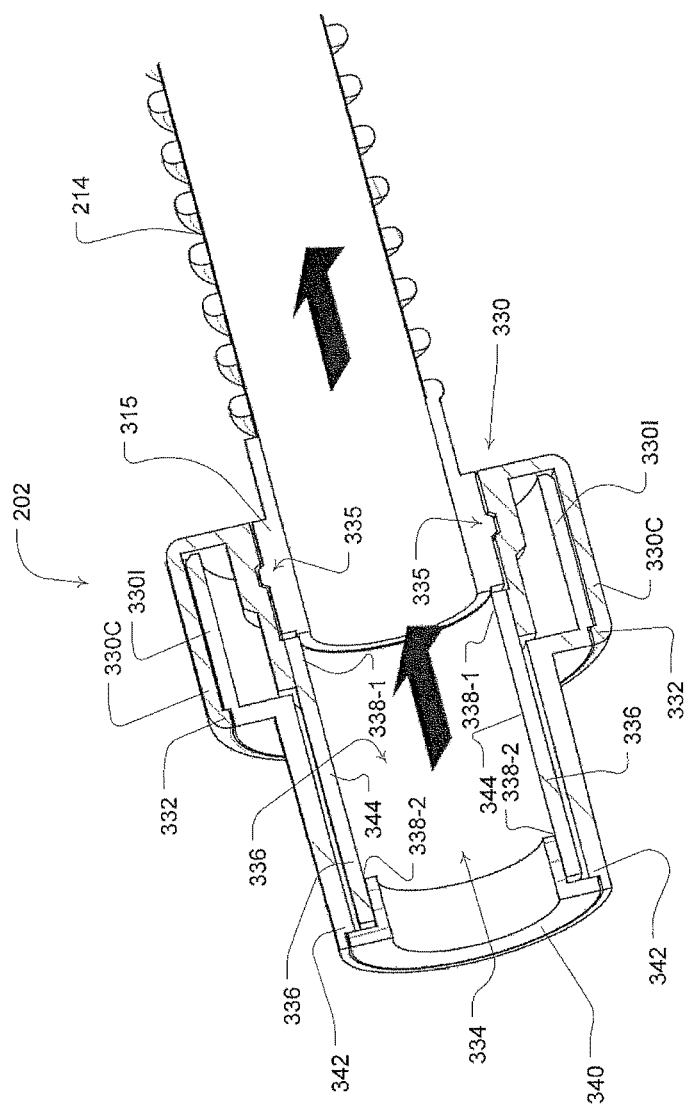
FIG. 3 is a cross-sectional illustration of the flow interrupter of FIG. 2, the flow interrupter being in an open configuration.
Figure 4:
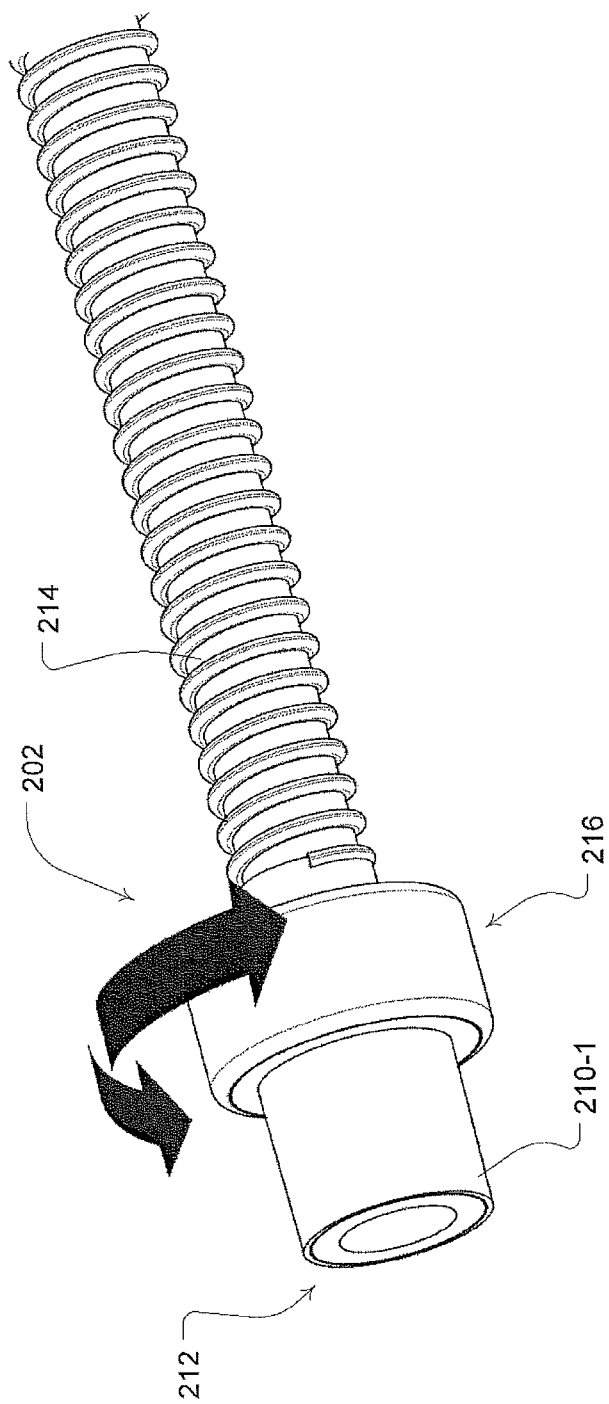
FIG. 4 illustrates a rotation operation of the flow interrupter of FIG. 2.

A cross-sectional view of the example flow interrupter component of FIG. 2 is shown in FIG. 3. In this example, the flow interrupter 202 is implemented with a swivel 330 to permit rotational operation of the flow interrupter. The swivel may be formed by two swivel members, the inner cylindrical member 330I and an outer cuff member 330C. A portion of the inner cylindrical member 330I may be retained within the outer cuff member 330C by a lip portion 332. The inner cylindrical member 330I and outer cuff member 330C are suitably sized and made of a suitably rigid material with smooth surfaces so that they can rotate with respect to each other. As shown in FIG. 3, the inner cylindrical member 330I can rotate within the outer cuff member 330C. The components of the swivel may serve as a manipulator for manually interrupting flow through the channel 334 of the swivel. Optionally, a portion of the swivel, such as the outer cuff member 330C may include or be formed with a coupler portion 335 for connection with a connection end 315 of the conduit 214 extension. Such a coupler portion is arranged for a free swivel type rotation around the connection end 315 of the conduit 214. The connection between swivel 330 and the connection end 315 of the conduit 214 is facilitated by a circular groove formed in the coupler portion 335 that engages a corresponding peripheral ridge formed on the surface of connection end 315.

As illustrated in FIG. 3, the flow interrupter may include a flexible wall 336 that serves as a portion of the gas passage channel of the flow interrupter. Since the interpreter is connected somewhere within the gas supply chain between the flow generator 104 and the patient interface 106, the flexible wall 336 effectively forms a portion of the gas supply channel of the respiratory system. The flexible wall 336 may be configured as a sleeve or a flexible cylinder within which flow may be interrupted. Typically, the flexible wall 336 may be affixed, in part, to the components of the swivel, such as at the opposing ends shown in FIG. 3 as first sleeve end 338-1 and second sleeve end 338-2. For example, they may be adhered with an adhesive or other suitable retention component or process. In this regard, the sleeve ends may be affixed to separate parts, one or more of which may be moveable, of the swivel that each provide a distinct rigid structure for the ends of the sleeve. For example, the first sleeve end 338-1 may be affixed to a portion of the outer cuff member 330C and the second sleeve end 338-2 may be fixed to a portion of the inner cylindrical member located at the end of the inner cylindrical member that is opposite to the end engaging the outer cuff member 330C.

In the example of FIG. 3, the second sleeve end 338-2 may be affixed to an optional adapter insert 340 which in turn may be fixably seated within an end seat 342 of the inner cylindrical member. In addition to its affixing function, the adapter insert 340 may also serve as a connector for connecting to a patient interface, a flow generator or a conduit.

With respect to the flexible wall, in a central portion 344 of the sleeve, between the affixed ends, the flexible wall may remain detached from the swivel components such that it may be generally free to move away from the rigid structural components of the swivel. For example, the flexible wall 336 may be configured to collapse, between the opposing ends, such that the central flexible wall of the sleeve may selectively block the channel by collapsing.

In one example, the flexible wall may be formed of a stretchable material, such as a thin rubber or other similar material. By rotation of either one of the inner cylindrical member or the outer cuff member with respect to the other, one end of the sleeve will rotate while the other will remain relatively stationary. Optionally, in the case of rotation of both of the inner cylindrical member or the outer cuff member in opposite directions, the sleeve ends will rotate in opposite directions. In either case, a central material portion of the flexible wall will collapse inwards and may twist into itself and thereby collapse the channel. With sufficient twisting of the flexible wall of the sleeve, the channel of the sleeve will close.

Figure 5:
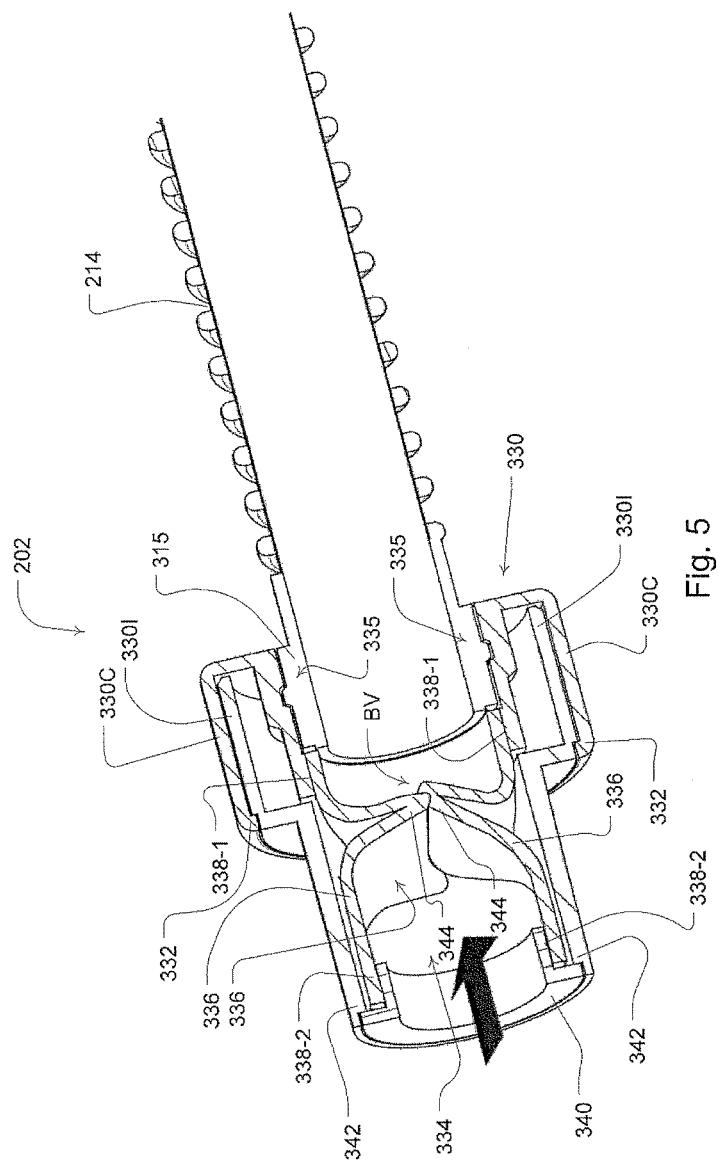
FIG. 5 is a cross-sectional illustration of the flow interrupter of FIG. 2 with the flow interrupter being in an closed configuration.

An example of such a rotation and twisting operation may be further considered in conjunction with FIGS. 4, 5, 6A and 6B. In the example, the outer cuff member may be manipulated by rotation in a direction of any one of the arrows indicated in FIG. 4, while the coupler 210-1, which is formed by the outer surface of a portion of the inner cylindrical member 330I, is kept stationary or is rotated in the opposite direction. As shown in FIG. 5, the rotation of, for example, the outer cuff member 330C in turn rotates a fixed end of the flexible wall (e.g., first sleeve end 338-1) relative to the other fixed end. Due to the connection ends as previously described and the swivel configuration, the outer cuff member can freely rotate independent of the conduit 214 attached to the flow interrupter. Moreover, the conduit 214 may be rotated without activating a closure of the flexible wall. If both ends of the flow interrupter need to be connected to conduits, a similar arrangement can be implemented at the other end of the flow interrupter so that the outer cuff member can freely rotate, independently of both conduits.

Figure 6A:
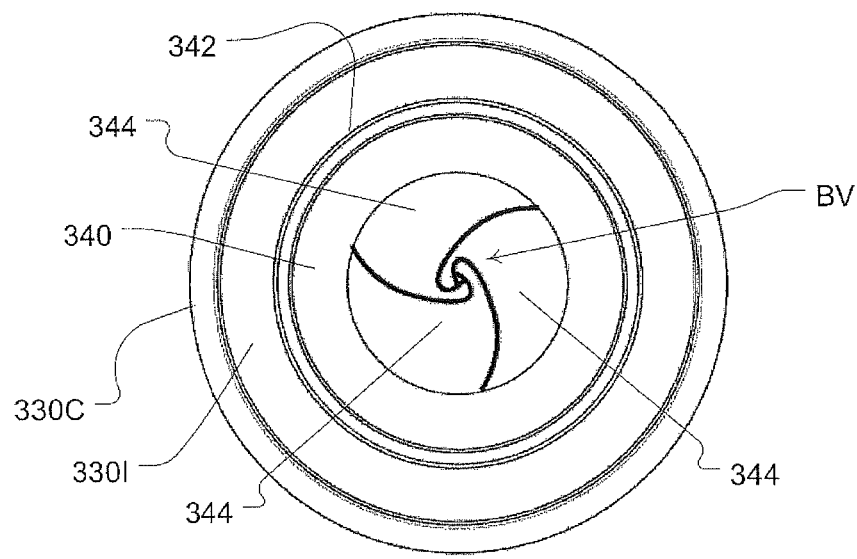
FIGS. 6A and 6B are end views of a flow interrupter showing the flow interrupter in a closed configuration and open configuration respectively.
Figure 6B:
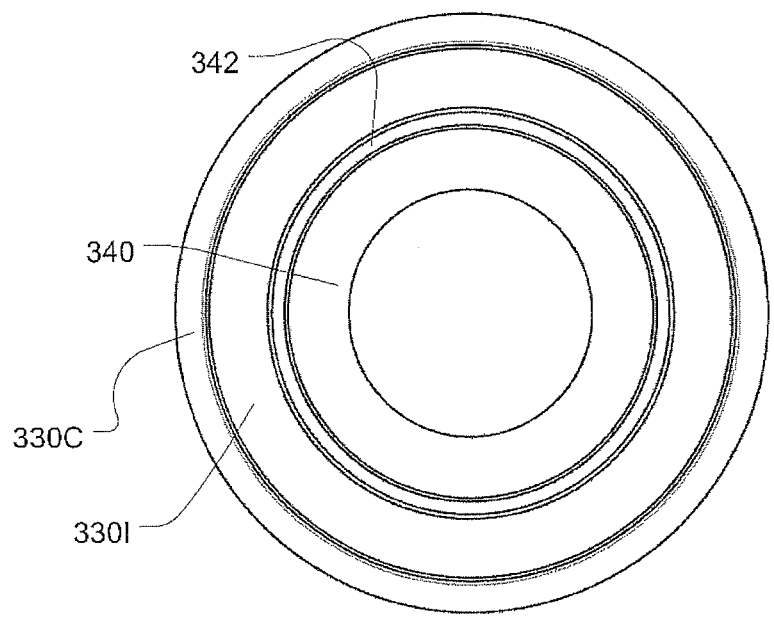

With the rotation of the outer cuff member with respect to inner cylindrical member, the flexible wall may then stretch at a central portion 344. Due to the fixed ends, it may thereby form a shape similar to an hour glass and may thereby cause a reduction in flow through the channel as the channel size is reduced. With further rotation, the flexible wall may bind with itself to form a bound vortex closure of stretched flexible wall material (shown as BV in FIGS. 5 and 6A). The bound vortex closure may then prevent or impede flow through the collapsed channel. By reversing the rotation of the outer cuff member, the flexible wall material will unwind to open the vortex closure and permit flow to resume through the channel as shown in FIG. 6B without the vortex closure.

In some cases, the flexible wall may be formed of a resilient material. In such cases, the rotation of the outer cuff member relative to the inner cylindrical member, and the consequent stretching of the material to form the vortex closure, may load an axial elastic force into the sleeve of the flexible wall. This resiliency force may then serve to permit an automatic re-opening (e.g., a reverse rotation of the outer cuff member relative to the inner cylindrical member) of the channel when the outer cuff member is simply released by a user. In such a case, a user would not need to actively open the channel. Such a resiliency of the material can thereby permit the channel of the flow interrupter to maintain a normally open characteristic. This may also avoid inadvertent closure of the flow interrupter. However, in some embodiments, the flow interrupter may include an optional detent mechanism (not shown) to selectively prevent rotation of the outer cuff member with respect to the inner cylindrical member. In such cases, the detent mechanism may be implemented with one or more positions to serve as a lock to prevent closure and/or opening of the channel of the flow interrupter unless the detent mechanism is unlocked from any receiving groove or the detent. In such cases, the detent and receiving groove may be components of the cylindrical member and cuff member respectively or vice versa.

Although the outer circumference of the outer cuff member and the outer surface of the inner cylindrical member are shown in the figures as having smooth surfaces, in some embodiments, these surfaces may include one or more ridges or other protrusion(s) to provide a user with a better grip or leverage for manipulating the flow interrupter. Such a protrusion (not shown), for example, formed on the outer surface of the inner cylindrical member, may permit a user to hold the outer cuff member in the palm of the hand, while turning the inner cylindrical member with respect to the outer cuff member, with the thumb of the same hand. The protrusion may be in the shape of a lug, a lever, a rib or have a more complex form and larger surface. At least a portion of the exposed surface of either of the outer cuff member or the outer surface of the inner cylindrical member may be formed in a way that will facilitate gripping. A single handed manipulation of the flow interrupter can make operation of the apparatus more convenient.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" have been used herein, unless otherwise specified, the language is not intended to provide any specified order but merely to assist in explaining distinct elements of the technology.

Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The invention claimed is:

1. An apparatus arranged for inclusion in a gas supply channel of a respiratory treatment system for selectively interrupting a flow of a breathable gas through the channel, the apparatus comprising:
    a hand operated swivel including first and second swivel members each being rotatable with respect to the other, the first swivel member comprising an outer cuff member and the second swivel member comprising an inner cylindrical member, the outer cuff member extending around a portion of the inner cylindrical member, the outer cuff member configured to be grasped and rotated by a hand; and
    a flexible wall comprising a first end fixed to the outer cuff member and a second end fixed to the inner cylindrical member, the outer cuff member and the inner cylindrical member both extending around the first end of the flexible wall, the flexible wall being arranged to, upon inclusion of the apparatus with the respiratory treatment system, form a portion of the gas supply channel;
    wherein a rotation of either one of the swivel members with respect to the other collapses the flexible wall between the first and the second end to reduce or interrupt the breathable gas flow through the gas supply channel, thereby moving the flexible wall from an open position to a collapsed position, and
    wherein the flexible wall is configured to store energy when the outer cuff member rotates to move the flexible wall to the collapsed position, and the apparatus is configured to automatically move, by the stored energy, the flexible wall from the collapsed position to the open position when a user releases the outer cuff member.

2. The apparatus of claim 1 wherein the flexible wall comprises a sleeve.

3. The apparatus of claim 1 wherein the flexible wall is configured to twist with rotation of the swivel to reduce the breathable gas flow through the channel.

4. The apparatus of claim 1 wherein the flexible wall is configured to twist with rotation of the swivel to close the channel and interrupt the breathable gas flow through the channel.

5. The apparatus of claim 1 wherein the flexible wall is configured to stretch with rotation of the swivel members with respect to each other.

6. The apparatus of claim 1 wherein the cuff member is adapted to retain a portion of the inner cylindrical member.

7. The apparatus of claim 1 further comprising a coupler at a first end of the apparatus for coupling with a breathable gas inlet of a patient interface, and a connector at a second end of the apparatus for coupling with a breathable gas outlet of a flow generator.

8. The apparatus of claim 7 wherein the patient interface comprises a respiratory mask.

9. The apparatus of claim 1 wherein the swivel comprises a lock to selectively prevent rotation of the swivel members.

10. The apparatus of claim 1 wherein the apparatus is integrally connected to a conduit arranged for connection to an inlet of a patient interface or an outlet of a flow generator.

11. The apparatus of claim 1 wherein the flexible wall and swivel are adapted to collapse the flexible wall to form a bound vortex closure of flexible wall material.

12. The apparatus of claim 1, wherein at least one of the swivel members comprises a protrusion arranged to facilitate a single handed manipulation of the apparatus.

13. The apparatus of claim 1 wherein the outer cuff member, the inner cylindrical member, and the flexible wall define a fixed length of the flexible wall between the first and second ends, the outer cuff member and the inner cylindrical member being configured to maintain the fixed length of the flexible wall when the outer cuff member is rotated.

14. The apparatus of claim 1 wherein the swivel further comprises a coupler portion configured for connection with a breathable gas conduit for free swivel type rotation of the coupler portion with respect to the breathable gas conduit.

15. An apparatus for selectively interrupting a flow of a breathable gas through a respiratory conduit, the apparatus comprising:
    a conduit having a passage to conduct the breathable gas, the passage traversing through a flexible wall sleeve, the flexible wall sleeve comprising a first end and a second end, and
    a manipulator attached to the flexible wall sleeve, the manipulator comprising an outer cuff member and an inner cylindrical member each being rotatable with respect to the other, the outer cuff member extending around a portion of the inner cylindrical member, the outer cuff member configured to be grasped and rotated by a hand;
    wherein the first end of the flexible wall sleeve is fixed to the outer cuff member and the second end of the flexible wall sleeve is fixed to the inner cylindrical member, the outer cuff member and the inner cylindrical member both extending around the first end of the flexible wall sleeve, and the flexible wall sleeve is adapted to twistably collapse between the first and second ends so as to reduce the passage by operation of the manipulator, thereby moving the flexible wall sleeve from an open position to a collapsed position, and wherein the flexible wall sleeve is configured to store energy when the outer cuff member rotates to move the flexible wall sleeve to the collapsed position, and the apparatus is configured to automatically move, by the stored energy, the flexible wall sleeve from the collapsed position to the open position when a user releases the outer cuff member.

16. The apparatus of claim 15 wherein the manipulator comprises a swivel.

17. The apparatus of claim 15 wherein the cuff member is adapted to retain a portion of the inner cylindrical member.

18. The apparatus of claim 15 wherein the flexible wall sleeve is configured to twist with rotation of the manipulator to reduce the passage.

19. The apparatus of claim 15 wherein the flexible wall sleeve is configured to twist with rotation of the manipulator to close the passage.

20. The apparatus of claim 15 wherein the flexible wall sleeve is configured to stretch with rotation of the manipulator.

21. The apparatus of claim 15 further comprising a coupler at a first end of the apparatus for coupling with a breathable gas inlet of a patient interface, and a connector at a second end of the apparatus for coupling with a breathable gas outlet of a flow generator.

22. The apparatus of claim 21 wherein the patient interface comprises a respiratory mask.

23. The apparatus of claim 15 wherein the manipulator comprises a lock to selectively prevent rotation of the manipulator.

24. The apparatus of claim 15 wherein the conduit comprises an outlet of a flow generator of a respiratory treatment apparatus.

25. The apparatus of claim 15 wherein the flexible wall sleeve and manipulator are adapted to collapse the flexible wall sleeve to form a bound vortex closure of stretched wall material.

26. The apparatus of claim 15 wherein the outer cuff member, the inner cylindrical member, and the flexible wall sleeve define a fixed length of the flexible wall sleeve between the first and second ends, the outer cuff member and the inner cylindrical member being configured to maintain the fixed length of the flexible wall sleeve when the outer cuff member is rotated.

27. The apparatus of claim 15 wherein the outer cuff member further comprises a coupler portion configured for connection with a breathable gas conduit for free swivel type rotation of the coupler portion with respect to the breathable gas conduit.

28. A method for selectively interrupting a flow of a breathable gas through a gas supply channel, the method comprising:

providing an apparatus arranged for inclusion in a gas supply channel of a respiratory treatment system for selectively interrupting a flow of a breathable gas through the channel, the apparatus comprising:

a hand operated swivel including first and second swivel members each being rotatable with respect to the other, the first swivel member comprising an outer cuff member and the second swivel member comprising an inner cylindrical member, the outer cuff member extending around a portion of the inner cylindrical member, the outer cuff member configured to be grasped and rotated by a hand; and a flexible wall comprising a first end fixed to the outer cuff member and a second end fixed to the inner cylindrical member, the outer cuff member and the inner cylindrical member both extending around the first end of the flexible wall, the flexible wall being arranged to, upon inclusion of the apparatus with the respiratory treatment system, form a portion of the gas supply channel;

rotating either one of the swivel members with respect to the other to collapse the flexible wall between the first and the second end to reduce or interrupt the breathable gas flow through the gas supply channel.

29. The method of claim 28 wherein the gas supply channel automatically opens for breathable gas flow therethrough when the outer cuff member is released by a user.

* * * * *